(12) United States Patent
Schneider et al.

(10) Patent No.: US 11,986,392 B2
(45) Date of Patent: May 21, 2024

(54) ANCHORING DEVICES, SYSTEMS, AND METHODS FOR IMPLANTABLE DEVICE

(71) Applicant: Boston Scientific Scimed, Inc., Maple Grove, MN (US)

(72) Inventors: Lucas Schneider, Champlin, MN (US); Padraig J. Savage, Santa Rosa, CA (US); Matthew Rust, Windsor, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 125 days.

(21) Appl. No.: 17/553,198

(22) Filed: Dec. 16, 2021

(65) Prior Publication Data

US 2022/0192830 A1  Jun. 23, 2022

Related U.S. Application Data

(60) Provisional application No. 63/126,748, filed on Dec. 17, 2020.

(51) Int. Cl.
*A61F 2/24* (2006.01)
*A61B 17/064* (2006.01)

(52) U.S. Cl.
CPC .......... *A61F 2/2466* (2013.01); *A61F 2/2445* (2013.01); *A61B 2017/0649* (2013.01); *A61F 2220/0016* (2013.01); *A61F 2230/0091* (2013.01)

(58) Field of Classification Search
CPC ...... A61F 2/2442; A61F 2/2445; A61F 2/246; A61F 2/2466; A61B 2017/0649
See application file for complete search history.

(56) References Cited

U.S. PATENT DOCUMENTS

| 9,180,005 | B1 | 11/2015 | Lashinski et al. |
| 9,192,471 | B2 | 11/2015 | Bolling |
| 9,610,156 | B2 | 4/2017 | Lashinski |

(Continued)

FOREIGN PATENT DOCUMENTS

WO  2020011880 A1  1/2020

OTHER PUBLICATIONS

International Search Report and Written Opinion dated Mar. 23, 2022 for International Application No. PCT/US2021/063804.

*Primary Examiner* — William H Matthews
(74) *Attorney, Agent, or Firm* — Seager, Tufte & Wickhem, LLP

(57) ABSTRACT

An anchor assembly having a helical anchor extending through an anchor bore defined in the anchor housing. In some embodiments, at least one helical turn of the helical anchor extends beyond a portion of the anchor bore. In some embodiments, at least one helical turn of the helical anchor extends beyond a side wall of the anchor housing. In some embodiments, the helical turns of the helical anchors of anchor assemblies mounted adjacent one another on an implantable device nest within one another when the implantable device is in an unexpanded configuration. In some embodiments, the distalmost helical turn of the helical anchor has an outer diameter greater than more proximal helical turns of the helical anchor. In some embodiments, the outer diameters of the at least some of the helical turns of the helical anchor taper from a distal end to a proximal end of the helical anchor.

20 Claims, 7 Drawing Sheets

(56) References Cited

U.S. PATENT DOCUMENTS

| | | |
|---|---|---|
| 9,795,480 B2 | 10/2017 | Bolling et al. |
| 9,848,983 B2 | 12/2017 | Lashinski et al. |
| 10,321,999 B2 | 6/2019 | Glenn et al. |
| 10,335,275 B2 | 7/2019 | Lashinski et al. |
| 10,548,731 B2 | 2/2020 | Lashinski et al. |
| 10,555,813 B2 | 2/2020 | Lashinski et al. |
| 2010/0249920 A1 | 9/2010 | Bolling et al. |
| 2016/0361168 A1* | 12/2016 | Gross .................... A61F 2/2466 |
| 2020/0022811 A1 | 1/2020 | Griswold et al. |
| 2020/0121461 A1 | 4/2020 | Bruner et al. |
| 2020/0383783 A1 | 12/2020 | Anderson et al. |
| 2021/0000600 A1 | 1/2021 | Inouye et al. |
| 2021/0220130 A1* | 7/2021 | Rajagopal ............. A61F 2/2466 |

* cited by examiner

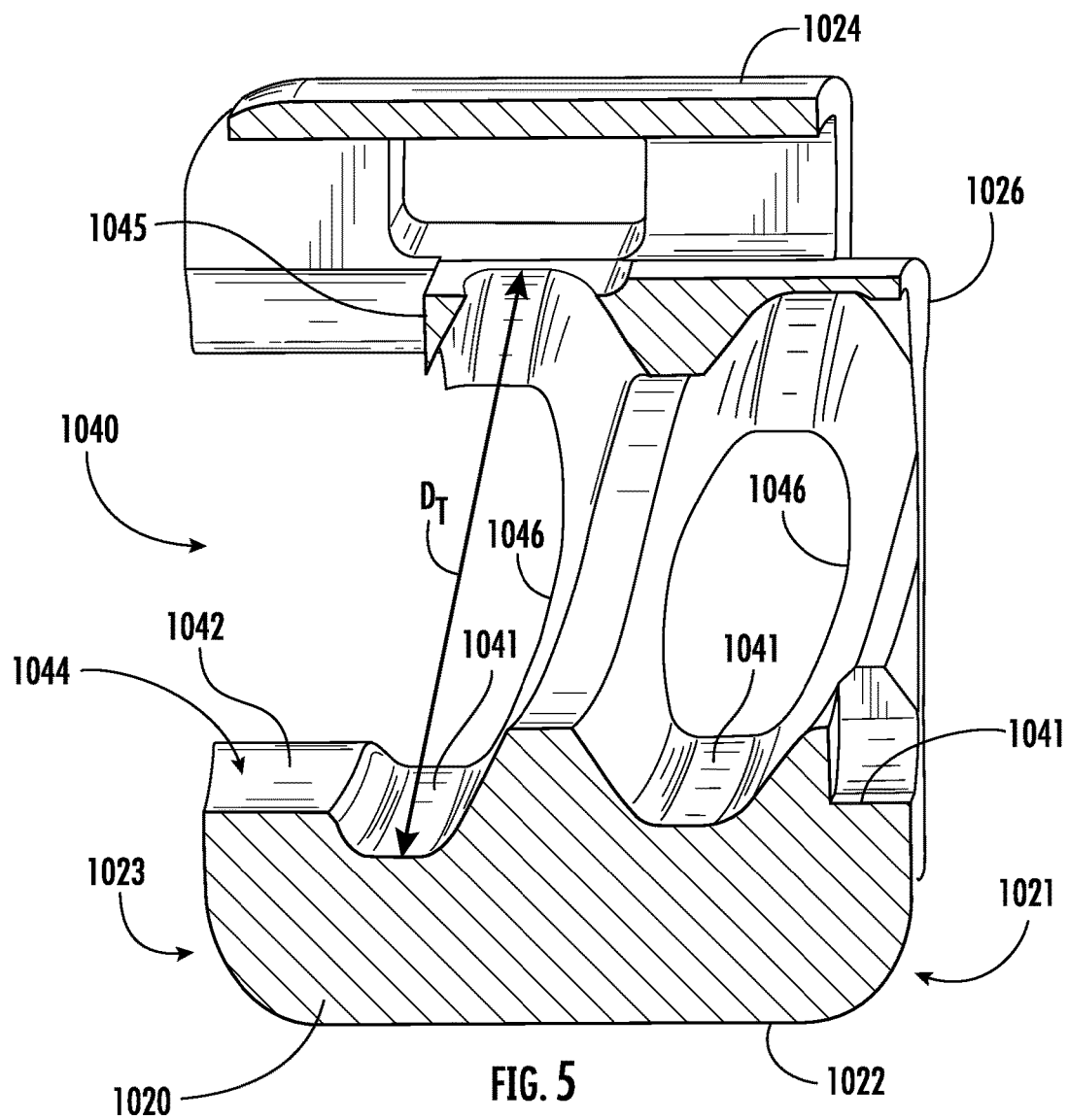
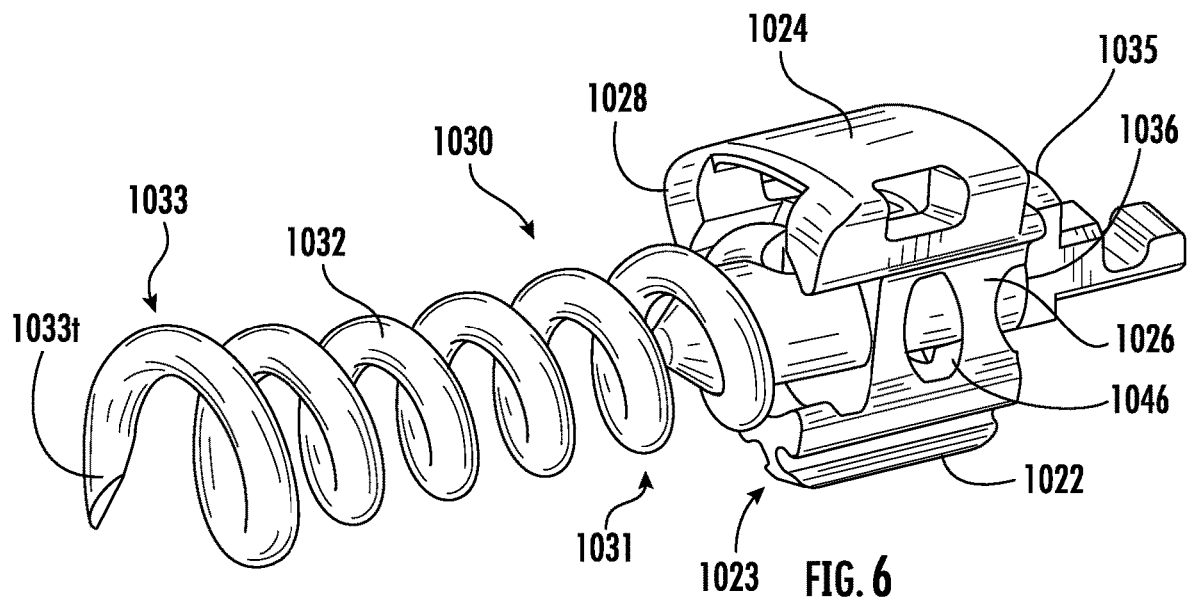

ANCHORING DEVICES, SYSTEMS, AND METHODS FOR IMPLANTABLE DEVICE

PRIORITY

The present application is a non-provisional of, and claims the benefit of priority under 35 U.S.C. § 119 to, U.S. Provisional Application Ser. No. 63/126,748, filed Dec. 17, 2020, the disclosure of which is hereby incorporated herein by reference in its entirety for all purposes.

FIELD

The present disclosure relates generally to the field of implantable medical devices. In particular, the present disclosure relates to improvements to anchoring devices, assemblies, and methods for use with implantable medical devices, such as for annuloplasty.

BACKGROUND

Mitral insufficiency (MI) (also known as mitral regurgitation or mitral incompetence) is a form of heart disease where the mitral valve leaflets no longer effectively close, or coapt, during systolic contraction. Regurgitation (backward flow into the atrium) of blood occurs during ventricular contraction and cardiac output may decrease as a result. Various surgical and endoluminal annuloplasty techniques, including transcatheter repair, for repairing or restoring a mitral valve to its native or an improved configuration include implanting an annuloplasty ring or other implantable device around the valve annulus. It is generally desirable to deliver an annuloplasty device in a minimally invasive manner (e.g., percutaneously and endoluminally, such as transfemorally, transeptally, or transapically). However, various structural components have interfered with reductions to the size of a collapsed annuloplasty device.

Improvements to annuloplasty devices allowing the desired or needed compact delivery size while enhancing or increasing retention or securement to the heart valve (e.g., the annulus) would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an anchor assembly includes a helical anchor having a plurality of helical turns, and an anchor housing with an anchor bore defined therein having internal threads through which the helical turns of the helical anchor extend. The helical anchor has a proximal end and a distal end, the distal end extending away from the anchor housing as the helical anchor is advanced distally away from the anchor housing. The distalmost helical turn of the helical anchor, closest to the distal end of the helical anchor, has an outer diameter greater than a diameter of at least a portion of the anchor bore.

In some embodiments, the helical anchor includes a shaft having a proximal end and a distal end, an anchor head along a proximal end of the shaft, and a helical coil having a proximal end and a distal end and defining the helical turns of the helical anchor, the proximal end of the helical coil mounted proximate the shaft distal end.

In some embodiments, the helical turns extend through openings in a side wall of the anchor housing.

In some embodiments, the helical anchor has a distal end configured to penetrate tissue, and a proximal end. Additionally or alternatively, the outer diameter of the distalmost helical turn closest to the distal end of the helical anchor is greater than the outer diameter of more proximal helical turns closer the proximal end of the helical anchor. Additionally or alternatively, the outer diameters of the two distalmost helical turns are greater than the outer diameter of helical turns proximal thereto. Additionally or alternatively, the outer diameters of the two distalmost helical turns taper in a proximal direction. Alternatively, the outer diameters of helical turns proximal to the two distalmost helical turns are substantially constant. Alternatively, the outer diameters of the helical turns taper in a direction from the distal end to the proximal end of the helical anchor.

In some embodiments, the distal end of the helical anchor has a sharpened tip to penetrate tissue.

In accordance with various principles of the present disclosure, an implant system includes an implantable device movable between an unexpanded configuration for delivery to a treatment site and an expanded configuration; and at least two anchor assemblies mounted on the implantable device adjacent one another. Each of the anchor assemblies may include a helical anchor with a plurality of helical turns, and an anchor housing with an anchor bore defined therein. In an unexpanded configuration of the implantable device, helical turns of adjacent anchor assemblies nest with one another.

In some embodiments, the implantable device includes a frame member, and the anchor assemblies are mounted on an end of the frame member. In some embodiments, the frame member includes a proximal end and a distal end, the distal end including a plurality of distal apices, the at least two anchor assemblies being mounted on adjacent distal apices of the frame member. In some embodiments, the helical anchor has a proximal end and a distal end, the distal end extending away from the anchor housing as the helical anchor is advanced distally away from the anchor housing; and the outer diameter of the distalmost helical turn closest to the distal end of the helical anchor is greater than the outer diameter of helical turns closer the proximal end of the helical anchor. In some embodiments, the anchor housing includes a frame slot for receiving a distal apex of the frame member; the anchor housing as an inner diameter; the distalmost turn of the helical anchor has an outer diameter greater than the anchor housing inner diameter such that the distalmost turn extends into the frame slot; and the distal apex is positioned in the frame slot proximal to the distalmost turn of the helical anchor when the distalmost turn of the helical anchor is positioned extending into the frame slot.

In some embodiments, the helical anchor has a proximal end and a distal end, the distal end extending away from the anchor housing as the helical anchor is advanced distally away from the anchor housing; and the outer diameter of the distalmost helical turn closest to the distal end of the helical anchor is greater than the outer diameter of helical turns closer the proximal end of the helical anchor.

In some embodiments, the anchor bore has internal threads through which the helical turns of the helical anchor extend; and the distalmost helical turn has an outer diameter greater than a diameter of at least a portion of the anchor bore.

In some embodiments, the helical turns extend through openings in a side wall of the anchor housing.

In accordance with various aspects of the present disclosure, a method of delivering an implantable device includes mounting at least two anchor assemblies adjacent one another on an implantable device, each anchor assembly including an anchor housing and a helical coil, the implantable device having an outer diameter which may be varied between an unexpanded outer diameter and a larger expanded outer diameter; and moving the implantable device into an unexpanded configuration with the helical coils of adjacent anchor assemblies nesting with one another.

In some embodiments, the helical anchor of each of the anchor assemblies has a proximal end and a distal end, the distal end extending away from the anchor housing as the helical anchor is advanced distally away from the anchor housing; and the distalmost helical turn of the helical anchor, closest to the distal end of the helical anchor, has an outer diameter greater than a diameter of at least a portion of the anchor bore.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 5 is a cross-sectional view along line V-V of FIG. 4 through an anchor housing formed in accordance with various aspects of the present disclosure.

FIG. 6 is a distal end and side perspective view of an embodiment of an anchor assembly formed in accordance various aspects of the present disclosure.

DETAILED DESCRIPTION

Figure 1:
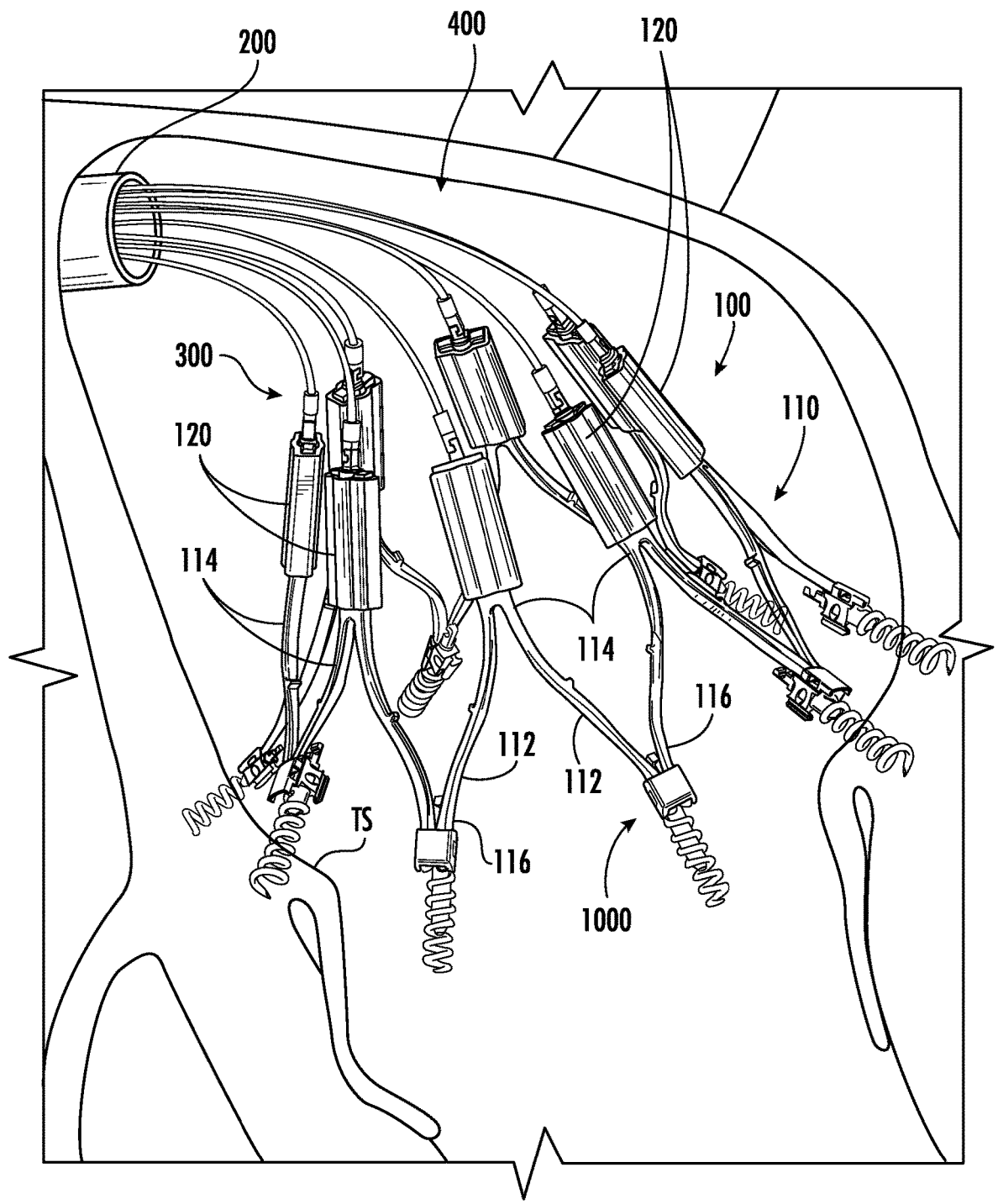
FIG. 1 is a schematic view of a human heart valve with an example of an implantable device with an anchoring assembly formed in accordance with various aspects of the present disclosure, the implantable device shown in a compact delivery configuration for delivery to the implant site.

The following detailed description should be read with reference to the drawings, which depict illustrative embodiments. It is to be understood that the disclosure is not limited to the particular embodiments described, as such may vary. All apparatuses and assemblies and systems and methods discussed herein are examples of apparatuses and/or assemblies and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

The present disclosure describes various embodiments of anchoring assemblies for an implantable device which is collapsible to a compact size for delivery. The implantable device may be sized for transluminal or endoluminal delivery, such as percutaneous delivery (including, without limitation, transfemoral, transseptal, and transapical delivery), to a treatment site (which may be alternately referenced as an implant site or site of implantation or the like, without intent to limit). The anchoring assembly described herein may be configured to fit within existing delivery devices (e.g., delivery tubes, catheters, sheaths, etc.). In some embodiments, the anchoring assemblies disclosed herein permit a more compact configuration than achieved in prior anchoring assemblies having similar components and structural features. In some embodiments, an anchor element disclosed herein is improved over prior anchor elements to enhance or increase retention within tissue in which the implantable device is to be implanted. It will be appreciated that the term anchor element is used for the sake of convenience and may be used interchangeably herein with terms such as anchor, anchor device, anchor mechanism, anchor component, anchoring element, anchoring device, anchoring mechanism, anchoring component, and the like, such terms being known in the art to represent structures configured to hold another object in place. It will further be appreciated that terms such as implant (and conjugations thereof) may be used interchangeably herein with terms (and conjugations thereof) such as affix, secure, couple, engage, anchor, hold, retain, etc., without intent to limit.

In accordance with various principles of the present disclosure, a collar-based anchoring assembly is provided with one or more anchor housings (such as in the form of a collar or sleeve or the like), the anchor housing having a bore or channel through which an anchor extends. The anchor housing may include structure for coupling the anchor assembly to the implantable device, such as by receiving a portion of the implantable device. In some aspects, the anchor housing is modified to reduce the collapsed size of the implantable device (when the implantable device is in a collapsed configuration, such as for delivery to a treatment site) relative to the collapsed size of prior implantable devices with functionally similar structural components and structural features.

An anchor housing formed in accordance with various principles of the present disclosure may be mounted to (such as at an end of) an annuloplasty device configured to be secured to and around a heart valve to reshape or reconfigure the valve. An anchor housing mounted on an annuloplasty device generally may be wedge-shaped to form a compact, generally circular, configuration when the implantable device is collapsed such as for delivery to a treatment site.

In accordance with various principles of the present disclosure, an anchoring assembly is provided with a helical anchor having a proximal anchor head, and a distal helical coil shaped for insertion into tissue at the treatment site. The bore of the anchor housing includes a threaded region with threads or grooves (such terms may be used interchangeably herein without intent to limit) receiving the helical turns or coils (such terms may be used interchangeably herein without intent to limit) of the helical coil. In accordance with some aspects of the present disclosure, two or more helical coils of the anchor have outer diameters that extend beyond the circumference of a portion of the bore and/or the threads in the anchor housing. More particularly, because the anchor housing may be wedge-shaped, the side walls of the anchor housing (generally radially extending walls as mounted on a generally tubular-shaped implantable device, and facing or adjacent to adjacent anchor housings on the implantable device) generally are not parallel to each other, and, instead, extend towards each other in a direction towards the center of the implantable device (in other words, in a direction radially inwardly of a generally tubular implantable device on which the anchor housing is mounted). As such, the distance between the side walls of the anchor housing varies from the outer perimeter of the anchoring assembly, as mounted on a generally tubular implantable device, towards the inner perimeter of the anchoring assembly. The anchor housing side walls may be spaced together such that the spacing of the inner surfaces of the side walls (such as at least at a location along the side walls closer to the radially inner side of the anchor housing) is less than the outer diameter of at least one of the helical coils of the anchor, such as a distalmost helical coil. The outer diameter of the at least one helical coil may extend beyond the wall (e.g., circumference) of the bore of the anchor housing at least at a location between the side walls closer to the radially inner side wall of the anchor housing than to the radially outer side wall of the anchor housing. It will be appreciated that reference to the outer diameter extending beyond the wall of the bore includes a threaded portion of the bore (receiving the helical coils of the anchor) and/or a nonthreaded portion of the bore. In some embodiments, the helical coil extends beyond the side walls, such as through openings within the side walls. In some embodiments, the entire length of the anchor coil extends past the anchor housing wall and/or past the anchor housing side walls.

In some embodiments, the turns of the helical coil are adjusted to fit a turn of one helical coil between two turns of an adjacent helical coil. Thus, helical coils of adjacent anchor assemblies may nest together (e.g., may be interposed) to allow a compact configuration of a collapsed implantable device on which a plurality of anchor assemblies formed in accordance with various principles of the present disclosure are mounted. Such nesting may permit the use of anchor housings narrower than the outer diameter of the helical coils without the helical coils of adjacent anchor housings interfering with one another. An implantable device with at least two such anchor assemblies adjacent one another may thus be placed in a compact configuration with an unexpanded outer diameter with helical coils of adjacent anchor assemblies nesting with one another.

In accordance with another aspect of the present disclosure, an anchoring assembly is provided with a proximally-tapered helical anchor with at least one and preferably at least two distal coils (further from the anchor head) having diameters greater than more proximal coils (closer to the anchor head). In some embodiments, the two distalmost coils of the helical anchor have diameters greater than the diameter of more proximal coils. The remaining coils of the helical anchor may further taper proximally, or may have substantially constant outer diameters. Such taper has been found to provide surprisingly improved performance, with dramatically better holding or retention strength than expected. Preclinical testing of helical anchors with at least two distalmost coils with diameters increased in accordance with principles of the present disclosure resulted in doubled pullout load, and a two to three times improvement of pullout load capability with over two weeks of healing as compared with prior art helical coils with a constant outer diameter.

In accordance with various principles of the present disclosure, an anchoring assembly is configured such that the helical coil of the anchor of the assembly extends through an internally threaded section in an anchor housing of the assembly. A shoulder may be provided between a threaded and an unthreaded section within the anchor housing to hold the helical anchor from proximal movement (such as axially) once all coils of the helical coil have advanced distally beyond the threaded section. In embodiments with a tapered helical coil as described above, the larger-diameter coils cannot extend into narrower more proximal internal threads within the anchor housing, thereby preventing proximal withdrawal of the helical anchor from the anchor housing (such as by rotation of the helical anchor). Alternatively, or additionally, the outer surface of the helical coil and/or the inner surface of the anchor housing bore may be configured to inhibit or prevent further proximal advancement of the helical coil relative to the anchor housing. A shoulder may be provided on the anchor head to abut the proximal end of the anchor housing (or a shoulder on the proximal end of the anchor housing) to inhibit further distal movement of the helical anchor relative to the anchor housing. The anchor is thereby held in place with respect to the anchor housing.

Various embodiments of anchoring devices, assemblies, and methods for implantable devices will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, in accordance with various principles of the present disclosure, at least one anchor assembly 1000 formed in accordance with various principles of the present disclosure may be provided on an implantable device 100 which is to be transported in a compact configuration through a tubular delivery device 200 (e.g., catheter or sheath or the like) such as for transluminal delivery (e.g., through the patient's vasculature system). In such case, particularly when more than one anchor assembly 1000 is provided, the anchor assembly 1000 must be designed with significant space constraints given the small size of the passages through which the implant system 400 (including, without limitation, the implantable device 100, anchor assembly 1000, and any associated delivery and deployment system 300) is to be transported. For instance, in some embodiments, the collapsed implant assembly (implantable device 100 including anchor assembly 1000) is to have an outer diameter of approximately 0.362" (0.919 cm) to fit within a working channel or delivery device lumen having an inner diameter of approximately 0.369" (0.937). However, it will be appreciated that slightly larger outer diameters of the collapsed implant assembly may be feasible, such as if delivered through a working channel or lumen with a degree of flexibility or elasticity, or with a larger inner diameter.

Figure 2:
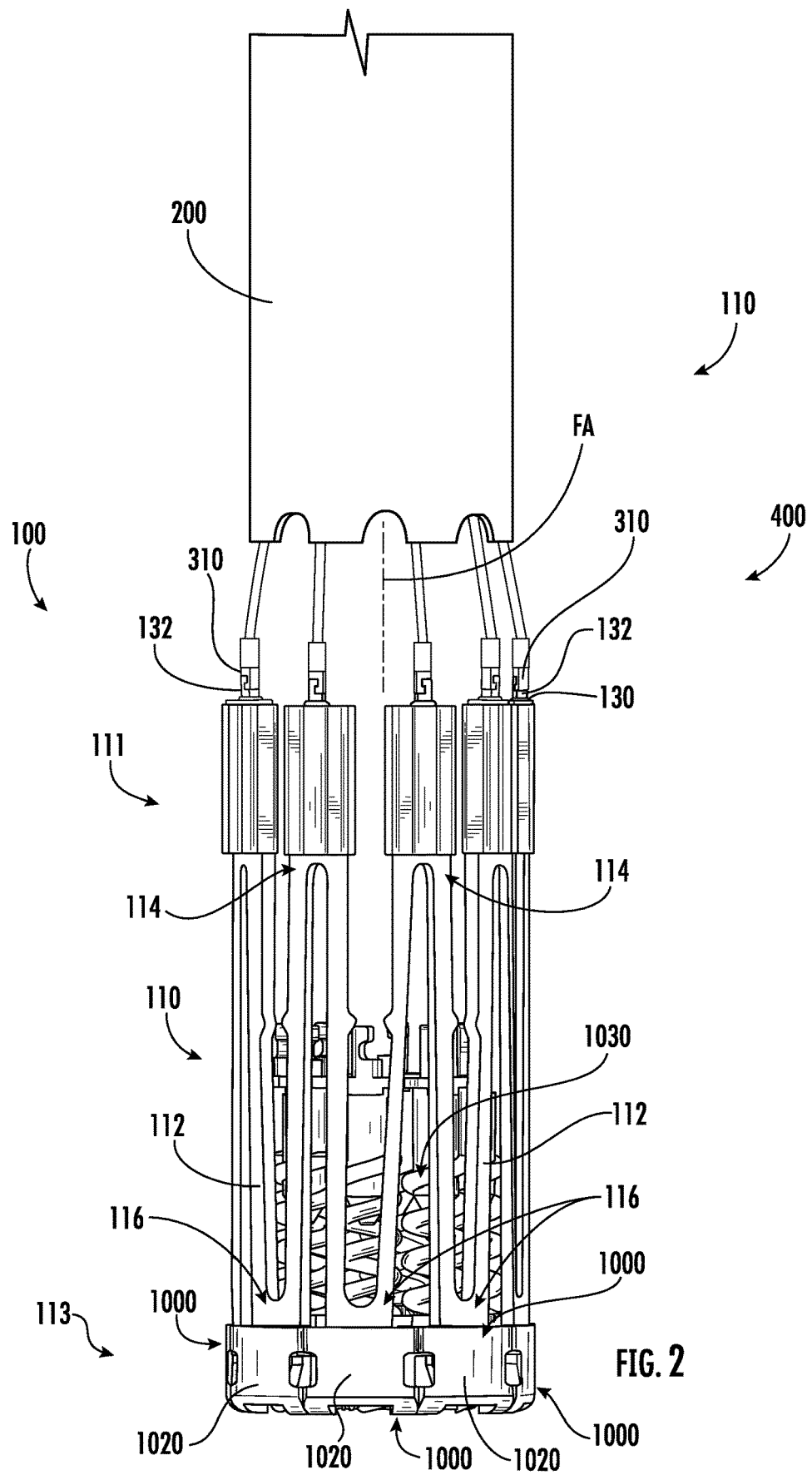
FIG. 2 is a perspective view of an example of an implantable device in a compact configuration in accordance with various principles of the present disclosure.

An example of an implantable device 100 which may benefit from an anchor assembly 1000 formed in accordance with principles of the present disclosure is an implantable annuloplasty device, such as for custom reshaping of a heart valve (e.g., the mitral valve, as illustrated, or the tricuspid valve) such as illustrated in FIGS. 1 and 2. The implantable device 100 may be configured to be delivered in a minimally invasive manner (e.g., percutaneously and endoluminally, such as transfemorally, transeptally, or transapically) in an unexpended (e.g., collapsed or compressed) configuration sized to fit within the delivery device 200 for delivery to the heart, such as illustrated in FIG. 1. The implantable device 100 may be expanded between the unexpanded and an operable expanded configuration (with a larger outer diameter than the outer diameter of the unexpanded configuration), once delivered to a heart valve annulus, either naturally (for example, if the frame is formed of a shape memory or super elastic material, such as Nitinol, that is biased towards an expanded state), or with the assistance of an expansion device or mechanism (for example, through the use of a force applied within the frame using an expandable deployment device, such as an inflatable balloon or the like). An imaging catheter 104 may be used to locate the treatment site TS at which the implantable device 100 is to be delivered/deployed and implanted and/or to observe the configuration and/or position of the implantable device 100 during implantation and adjustment. An example of a steerable delivery device and system with various positioning and imaging capabilities is described in U.S. Pat. No. 10,335,275, titled Methods For Deployment Of Heart Valve Devices Using Intravascular Ultrasound Imaging, and issued on Jul. 2, 2019, which patent is incorporated herein by reference in its entirety for all purposes.

Once delivered, the implantable device 100 is deployed and secured to the heart at the implantation site, such as with an anchor assembly 1000 as described herein. It will further be appreciated that terms such as secure (and conjugations thereof) with respect to an implantable device may be used interchangeably herein with terms (and conjugations thereof) such as affix, implant, couple, engage, anchor, hold, retain, etc., without intent to limit. The shape, size, dimension, configuration, etc. of the implantable device 100, once implanted, may then be adjusted to configure the shape and/or structure of the heart valve annulus VA to which the implantable device 100 is secured, as medically indicated. In the example of an implantable device 100 illustrated in FIGS. 1 and 2, the implantable device 100 includes a frame member 110 that may be disposed about and implanted in a heart valve or other cardiac feature once expanded. The frame member 110 may be generally symmetrical with respect to the central frame axis FA although it need not be symmetrical. The frame member 110 may form a generally tubular shape, the term "tubular" being understood herein to include circular as well as other rounded or otherwise closed shapes. As used herein, reference to the "circumference" of the frame member 110 is to be understood as referencing a perimeter or boundary and can refer to a circular or other rounded or non-rounded path lying in a plane substantially transverse to the frame axis FA. The frame member 110 may assume various shapes, sizes, dimensions, configurations, etc. during different phases of deployment such as during pre-delivery, delivery, tissue engagement, anchoring, adjustment (e.g., cinching), etc. For example, the frame member 110 may be configured to change shape, size, dimension, and/or configuration, such as to modify the shape, size, dimension, configuration, etc. of the valve annulus (or other structure) to which it is coupled.

The frame member 110 may be formed from one or more struts 112 that may form all or part of the frame member 110. The struts 112 may include elongated structural members formed of a metal alloy, a shape memory material, such as an alloy of nickel titanium or other metals, metal alloys, plastics, polymers, composites, other suitable materials, or combinations thereof. In one embodiment, the struts 112 may be formed from the same, monolithic piece of material (e.g., tube stock). Thus, reference to struts 112 may refer to different portions of the same, coextensive component. Alternatively, reference to struts 112 may refer to components that are formed separately and attached together (optionally permanently, such as by welding or other methods). In some embodiments, the struts 112 are coupled at proximal end 111 and distal end 113 of the frame member 110 to form, respectively, proximal apices 114 and distal apices 116. Alternatively, if formed from a monolithic piece of material, the material may be cut or otherwise formed to define proximal apices 114 and distal apices 116. In the illustrated embodiments, the proximal end 111 of the frame member 110 is directed proximally toward and engaged or carried by the delivery/deployment system 102, and the radially-distal end 113 of the frame member 110 extends distally from the delivery and deployment system 300 and is the end engaged with the treatment site TS. It will be appreciated that alternate configurations of the frame member 110, such as depending on the manner and orientation in which the implantable device 100 is delivered, are within the scope and spirit of the present disclosure.

The example of an implantable device illustrated in the figures may be considered to use collar-based adjustment mechanisms, such as a collar-based frame adjusting mechanism and a collar-based anchor assembly. For instance, a plurality of cinch collars 120 (which may be referenced or otherwise known as collars or sleeves or cinch sleeves or sliders or nuts, and such terms may be used interchangeably herein without intent to limit, reference being made generally to collars for the sake of convenience) are carried at the proximal end 111 of the frame member 110, such as along the proximal apices 114 of the frame member 110. Advancement or withdrawal of a collar 120 with respect to the proximal apex 114 over which the collar 120 is positioned adjusts the relative positions of the struts 112 joined at such apex. Each collar 120 preferably is adjustable independently of the other collars 120. Such adjustment results in adjustment of at least one of the size, shape, configuration, dimension, etc. of the frame member 110 (e.g., retraction/compression or expansion of the frame upon bringing adjacent struts 112 closer or further apart, respectively) to affect at least one of the size, shape, configuration, dimension, etc. of the treatment site TS (such as to restore or correct the shape of a valve annulus for proper functioning or competency thereof). The collars 120 may be adjusted in various manners, such as by engagement with a threaded collar actuator 130 engaging threads within the collars 120, rotation of the collar actuator 130 (held against axial movement) causing axial movement of the collars 120. A latch 132 may be provided on the collar actuator 130 for engagement by a latch of an actuator 310 provided to actuate (e.g., move, advance, retract, etc.) the collar 120 as desired.

Figure 3:
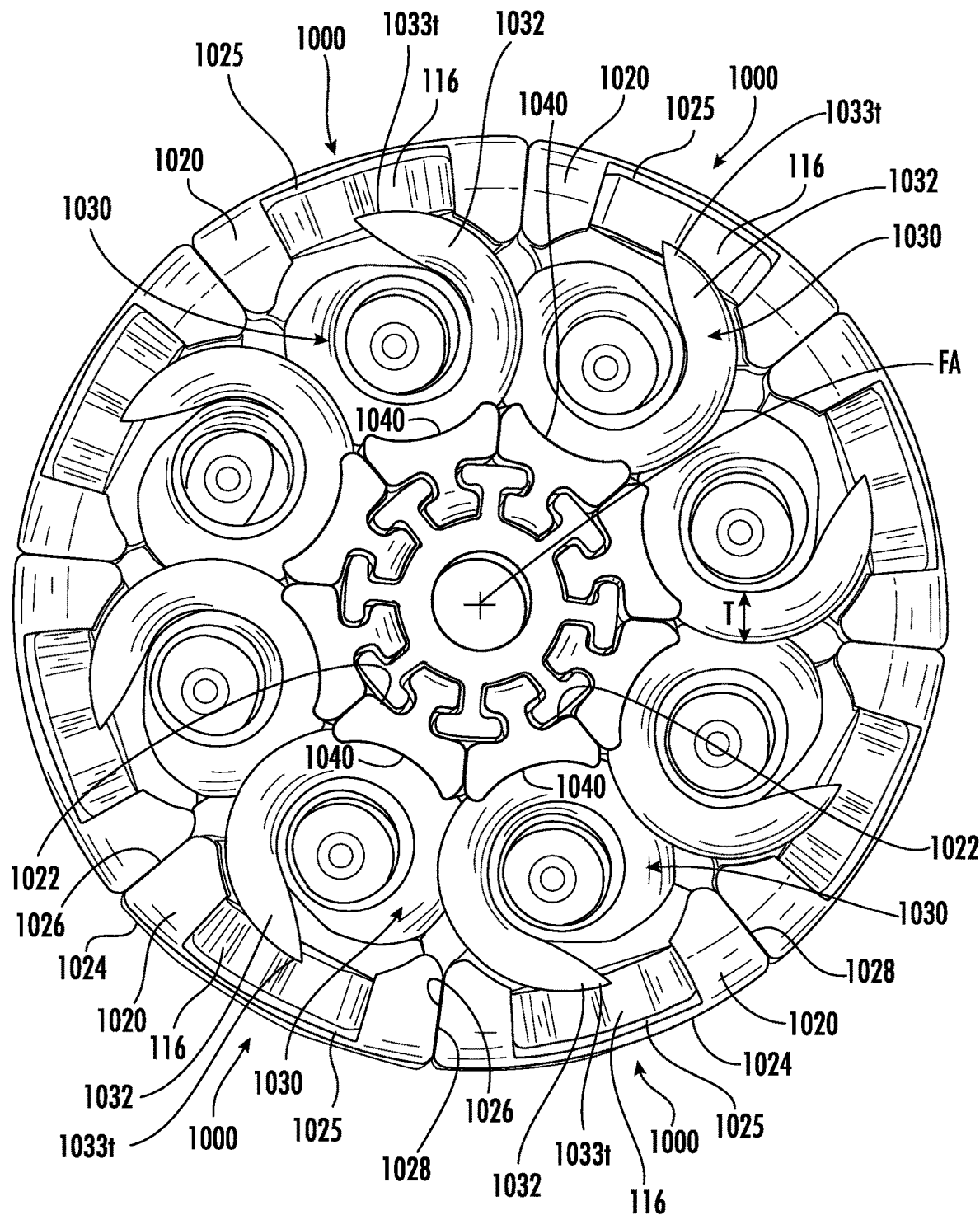
FIG. 3 is a distal end view of an implantable device such as in FIG. 2.

To facilitate anchoring of the implantable device 100 at the treatment site TS, one or more anchor assemblies 1000 are provided, such as at the distal end 113 of the frame member 110 of the implantable device 100. In accordance with various principles of the present disclosure, at least one of the anchor assemblies 1000 illustrated in FIGS. 1-3 is a collar-based anchor assembly including an anchor housing 1020 such as in the form of a collar (such term may be used interchangeably herein with the term sleeve or the like without intent to limit, reference generally being made to "anchor housing" for the sake of convenience). The anchor housing 1020 is configured to be coupled or otherwise mounted on or to the implantable device 100, such as on a distal apices 116 at the distal end 113 of the frame member 110 of the implantable device 100. In one embodiment, the anchor housing 1020 includes a frame slot 1025 (such term being used for the sake of convenience and may be used interchangeably herein with terms such as frame channel, frame sleeve, or the like, without intent to limit) configured to receive a portion of the frame member 110, such as a distal apex 116 thereof.

As illustrated in the end view of FIG. 3, when used with a generally circular frame member 110, the anchor housings 1020 may be wedge-shaped to achieve a compact configuration when the implantable device 100 is in a delivery configuration (e.g., collapsed or unexpanded or the like, such terms being used interchangeably herein without intent to limit). More particularly, each anchor housing 1020 has a radially-inwardly positioned inner wall 1022, a radially-outwardly positioned outer wall 1024 opposite the inner wall 1022, and a pair of opposing side walls 1026, 1028, each extending between the inner wall 1022 and the outer wall 1024. The inner wall 1022 is positioned closer to the frame axis FA than the outer wall 1024, and the side walls 1026, 1028 are closer to each other nearer the inner wall 1022 than the outer wall 1024, thereby forming a wedge-shape of the anchor housing 1020 when viewed from above or below (in an axial direction along the frame axis FA of the implantable device 100 on which the anchor housing 1020 is mounted). Although the frame slot 1025 is illustrated along an outer wall 1024 of the anchor housing 1020, other positions are within the scope and spirit of the present disclosure.

Figure 4:
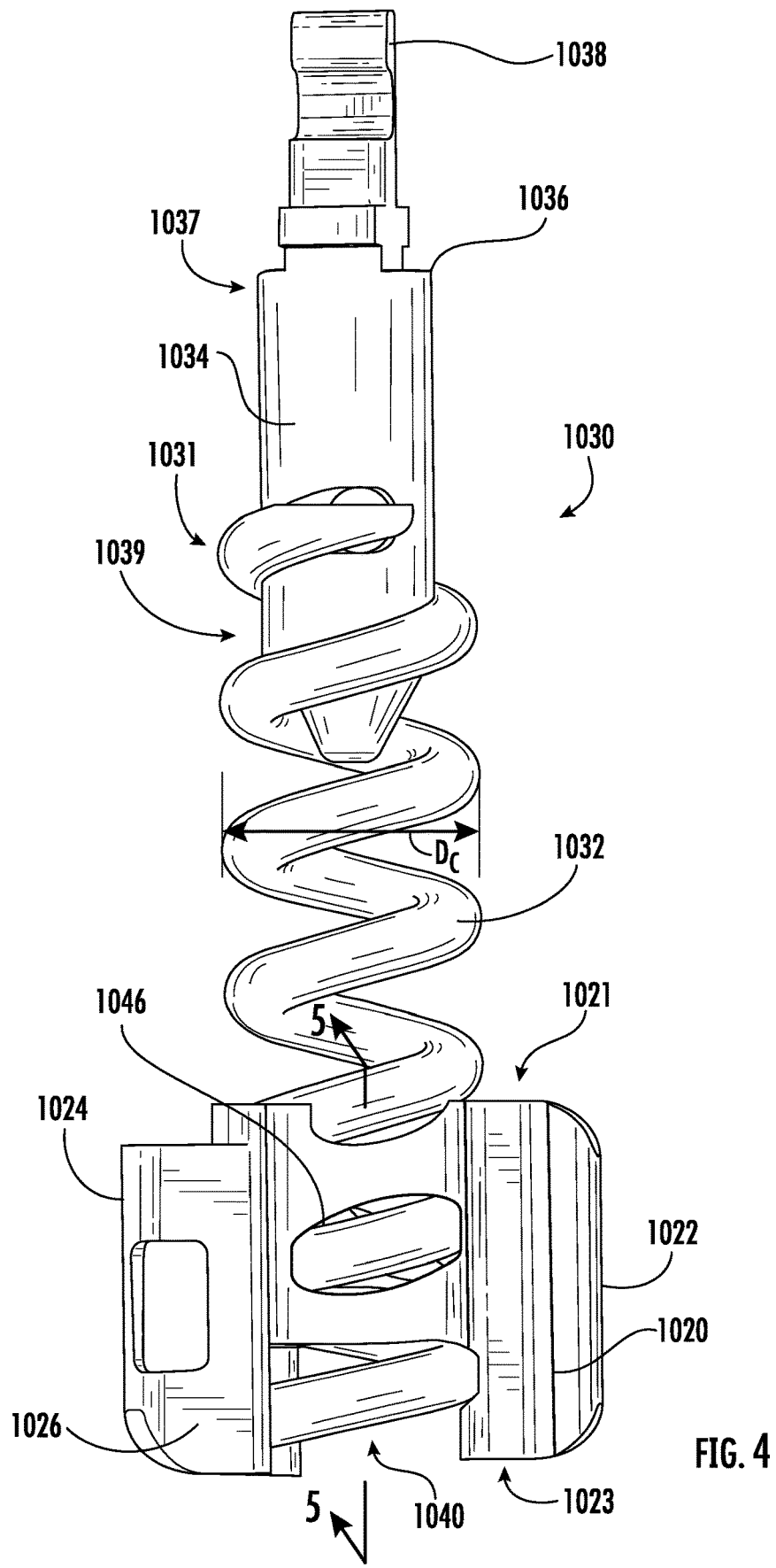
FIG. 4 is an elevational view of an embodiment of an anchor assembly formed in accordance with various aspects of the present disclosure.

In accordance with various aspects of the present disclosure, as may be appreciated with reference to FIGS. 2 and 3, an anchor assembly 1000 formed in accordance with various principles of the present disclosure, and as shown in isolation in FIG. 4, includes a helical anchor 1030 having a helical coil 1032 coupled proximate a distal end 1039 of an anchor shaft 1034 (e.g., with a proximal end 1031 of the helical coil 1032 mounted on the anchor shaft 1034). The distal end 1033 of the helical coil 1032 (the end which extends away from the anchor housing 1020 and leads entry of the helical coil 1032 into the treatment site TS to anchor the anchor assembly 1000 thereto) may have a sharpened distal tip 1033t to penetrate and to facilitate entry and advancement into tissue. The anchor shaft 1034 may include an anchor head 1036 at a proximal end 1037 thereof. The anchor head 1036 may be provided with a coupler 1038 configured to engage with an anchor latch 310 controllable at a proximal end by the medical professional implanting the implantable device 100 to hold the helical anchor 1030 in place during delivery to the treatment site TS.

The helical anchor 1030 rotationally advances or retracts through an anchor bore 1040 defined through (e.g., axially through) the anchor housing 1020, and may be guided by mating internal threads or grooves 1041 on the inner wall 1042 in the anchor bore 1040, as illustrated in FIG. 4 and FIG. 5. The anchor bore 1040 may include an unthreaded distal section 1044 (closer to the distal end 1023 of the anchor housing 1020) in which the proximal coils of the helical coil 1032 of the helical anchor 1030 may be positioned when the helical anchor 1030 is substantially fully deployed to allow for "free spin" of the anchor (drawing tissue proximally towards the anchor housing 1020 without advancing the helical anchor 1030 distally with respect to the anchor housing 1020).

As may be appreciated with reference to FIGS. 4 and 5, the outer diameter D of the helical coil 1032 may be greater than at least a portion of the diameter DT of the threads 1041 (if varying dimensions, as described below, then greater than at least the smaller of the thread diameters DT) in the anchor housing 1020. In some embodiments, such as illustrated, the helical turns of the helical coil 1032 extend beyond at least a portion of the threads 1041 (e.g., beyond a portion of a circumference of the threads 1041) and the inner wall 1042 of the anchor bore 1023, and even beyond the side walls 1026, 1028 of the anchor housing 1020, particularly along a region of the side walls 1026, 1028 closer to the inner wall 1022 of the anchor housing 1020 where the side walls 1026, 1028 are closer together (relative to the spacing of the side walls 1026, 1028 closer to the outer wall 1024 of the anchor housing 1020). In some embodiments, as illustrated in FIG. 4 (and also with reference to FIGS. 5 and 6), the helical turns of the helical coil 1032 may extend through an opening 1046 (which may be alternately referenced herein as an aperture or window or hole or the like, without intent to limit) in one or both of the side walls 1026, 1028 of the anchor housing 1020. As such, the anchor housing 1020 may have a reduced width (dimension between the side walls 1026, 1028) relative to an anchor housing without such an opening, such as prior anchor housings. By "breaking through" the anchor housing 1020, the helical coil 1032 portions of the helical anchors 1030 can nest with adjacent helical coils 1032 rather than being encapsulated by a larger sized anchor housing 1020, allowing for narrower anchor housings 1020 than prior anchor housings. Such nesting of adjacent anchors 1030 and reduction in the width of the anchor housing 1020 results in a more compact unexpanded configuration of the implantable device 100. For instance, a delivery device 200 may have an inner diameter of approximately 0.370 inches (0.094 cm), and the outer diameter of an implantable device 100 with anchor assemblies 1010 formed in accordance with principles of the present disclosure may have an overall outer diameter of approximately 0.362 inches (0.919 cm). The delivery device 200 may be formed to allow some degree of expansion (e.g., may be formed of a polymer and braided coil) such that even if there is not much clearance between the implantable device 100 and the anchor assemblies 1010, the delivery device 200 has some "give" to allow passage of the implant system 400, preferably held in a compact configuration, therethrough. In some embodiments, the delivery device 200 holds the implant system 400 in a compact configuration.

In some embodiments, the turns of the helical coil 1032 are sized, shaped, and/or configured to nest with the turns of adjacent helical coil 1032 of anchor assemblies 1000 mounted along the circumference of the implantable device 100, as may be appreciated with reference to FIG. 3. For instance, the pitch distance between turns of a helical coil 1032 and the thickness T of the element coiled to form the turns of the helical coils (such as a wire, or the thickness of threads of a threaded anchor shaft if used in place of a helical coil) may be selected to allow a turn of a coil of a helical coil 1032 to nest between turns of an adjacent helical coil 1032. For instance, the threads per inch of the helical coil 1032 may be reduced from a value of 25 threads per inch (in prior helical coils) to a value of 22 threads per inch, with a peak-to-peak distance increasing from approximately 0.040 inches (0.102 cm) (in prior helical coils) to approximately 0.045 inches (0.114 cm). The threads per inch and peak-to-peak distances are selected so that there is just enough distance between adjacent turns of the helical coil 1032 to fit a portion of a coil of an adjacent (neighboring) anchor therebetween, as ay be appreciated with reference to FIG. 3. It will be appreciated that the values provided herein may vary depending on such parameters as the thickness T of the coil (which may be referenced as the wire diameter of the coil, or, in other words, the element forming the individual turns of the helical coil 1032), the outer diameter of the helical coil 1032, and/or pull-out testing performance.

It will be appreciated that to accommodate an anchor assembly 1000 as described above, with helical coil 1032 extending beyond the threads 1041 and/or inner walls 1042 of the anchor bore 1023, and/or side walls 1026, 1028 of the anchor housing 1020, one or more modifications may be made to the implantable device 100, such as to the frame member 110 thereof. For instance, in some embodiments, an ideal position of the tip 1033t of the helical coil 1032 is along the outer wall 1024 of the anchor housing 1020, approximately midway between the side walls 1026, 1028 of the anchor housing 1020 (a 12 o'clock position). In the embodiment illustrated in FIG. 3, such position of the tip 1033t of the helical coil 1032 is adjacent to the frame slot 1025 and thus may interfere with the frame member's distal apex 116 extending through the frame slot 1025. It may be desirable in such embodiments to shorten the distal apex 116 (in comparison with those of prior similar frame members 110, or distal apices 116 not associated with an anchor housing 1020 of an anchor assembly 1000 as described above). In some embodiments, the distal apex 116 on which an anchor assembly 1000 formed as described above is shortened by approximately 0.050" (0.127 cm). It will be appreciate that other modifications to the frame member 110 are within the scope and spirit of the present disclosure as well.

Figure 7:
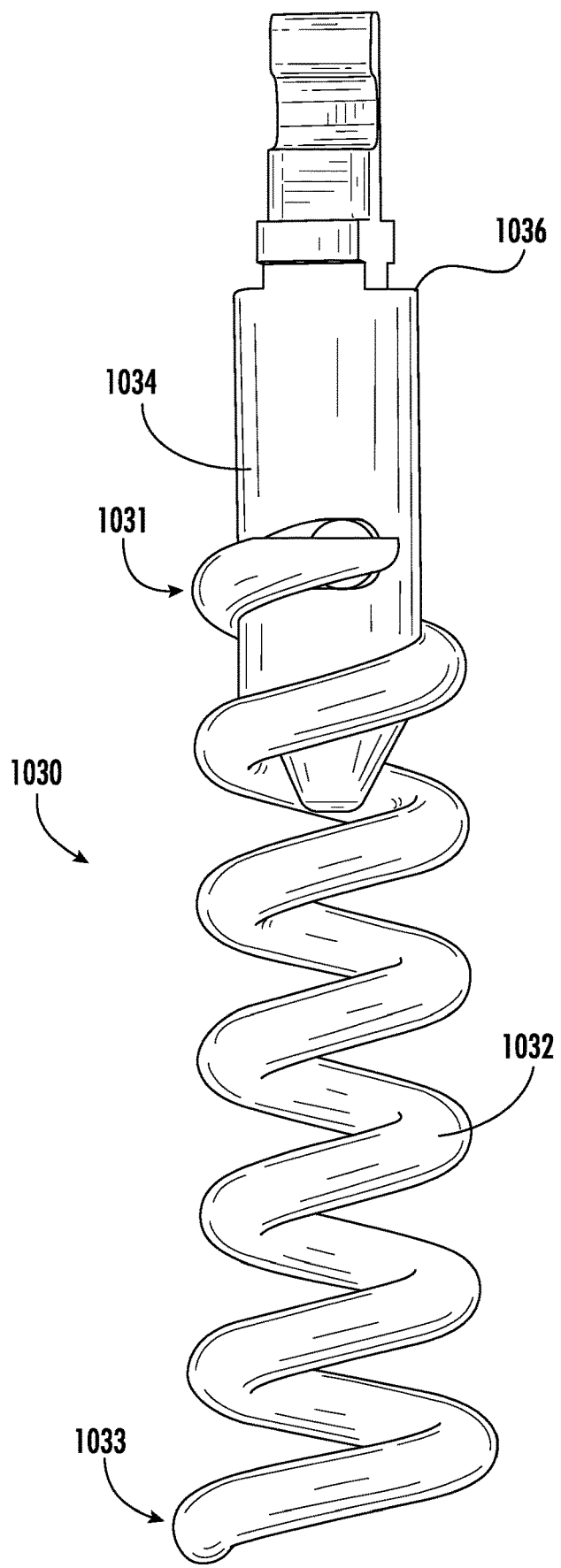
FIG. 7 is an elevational view of an embodiment of an anchor formed in accordance with various aspects of the present disclosure.

The outer diameter of the turns of the helical coil 1032 of anchor assemblies 1000 formed in accordance with principles of the present disclosure may be substantially constant along the length of the anchor 1030. In accordance with some aspects of the present disclosure, it has been discovered that an increase in the outer diameter D of the helical coil 1032 at a distal end 1033 of the helical coil 1032, such as a taper of the helical coil 1032 from the distal end 1033 in a direction towards the proximal end 1031 thereof (such as shown in FIG. 6 and FIG. 7) results in surprisingly increased performance of the anchor 1030, including dramatically improved anchor pull out loads (relative to prior art anchors). In some embodiments, a helical coil 1032 formed in accordance with various principles of the present disclosure has a taper of approximately 6 degrees (from the larger distal end 1033 of the helical coil 1032 in a direction towards the proximal end 1031 of the helical coil 1032). The taper may be as little as approximately 4 degrees to as much as approximately 12 degrees (including increments of 0.2 degrees therebetween). In some embodiments, a helical coil 1032 formed in accordance with various principles of the present disclosure has at least one coil at the distal end 1033 with an outer diameter larger than the outer diameter of proximal coils closer to the proximal end 1031 of the helical coil 1032 and closer to the anchor head 1036. In one embodiment of a helical coil 1032 formed in accordance with principles of the present disclosure, the outer diameter D of the helical coil 1032 is increased for the last two coil revolutions. The increase in diameter may be approximately 0.020 inches (0.508 mm)±0.001 inches (0.025 mm). For instance, in some embodiments, the outer diameter D of the proximal turns of the helical coil 1032 is approximately 0.080 inches (0.232 mm)±0.001 inches (0.025 mm) and the outer diameter D of the distalmost turn (or the two distalmost turns) of the helical coil 1032 is approximately 0.099 inches (2.514 mm)±0.001 inches (0.025 mm). It has been determined that increases in coil outer diameter provide improved pull-out strength, and the maximum coil outer diameter increase may be selected with reference to dimensions which allow the collapsed implant assembly to fit within a given working channel and/or delivery device lumen. The distalmost turn of the helical coil 1032 may have an outer diameter D greater than the outer diameter D of the adjacent more proximal coil. The outer diameters of the coils proximal to the distalmost coil, or proximal to the two distalmost coils, may be substantially constant or may be tapered, such as in a proximal direction. The pitch of the coils of the helical coil 1032 may remain substantially constant along the length of the helical coil 1032.

It will be appreciated that the threads 1041 within the anchor bore 1040 of an anchor housing 1020 of an anchor assembly 1010 accommodating an anchor 1030 with a helical coil 1032 with a substantially constant outer diameter D may have a substantially constant diameter. However, an anchor housing 1020 of an anchor assembly 1010 with a tapered helical coil 1032 may include tapered threads to correspond to the taper of the helical coil 1032, as may be appreciated with reference to FIG. 5. Such tapering may be selected such that the coils at the distal end 1033 of the helical coil 1032 (with larger outer diameters Dc than the outer diameters D of more proximal coils) may be accommodated within the anchor housing 1020 when the anchor assembly 1010 is delivered mounted on an implantable device 100 so that the distal tips 1033 of the helical coils 1032 (which may be sharp) are shielded or otherwise not exposed (e.g., within the confines of the anchor housing 1020, subsurface to the distal end 1023 of the anchor housing 1020). As such, the implant system 400 travels through the delivery device 200 in a generally atraumatic configuration, with substantially no sharp edges or surfaces. The taper of the threads 1041 of the anchor bore 1040 may be formed by a milling cutter with an axis (about which the cutting blade rotates) which is rotated through the anchor housing 1020 about a helical path with a varying diameter. The cutting edge may be along the radial edge of the fin of the cutting blade to perform such cutting, with the tip of the blade modified to correspond with the outer surface shape of the helical coil 1032 to be extended therethrough.

It will be appreciated that in accordance with an aspect of the present disclosure, the diameter of the threads 1041 of the anchor bore 1040 in the anchor housing 1020 may taper proximally to correspond to the proximal taper of the helical coil 1032 of the anchor 1030. Accordingly, in such embodiment, the distalmost thread of the helical coil 1032 will not be able to rotate proximally beyond the distalmost thread within the anchor bore 1040, and undesired or unintended proximal withdrawal of the helical anchor 1030 from the anchor housing 1020 may thereby be prevented. In contrast, if the helical coil 1032 has a constant outer diameter D, then the threads 1041 of the anchor bore 1040 may have constant diameters as well. In such embodiment, undesired or unintended proximal withdrawal of such an anchor 1030 may be prevented by adjusting the pitch between the distalmost turns of the helical coil 1032 thereof so that the distalmost threads cannot extend proximal to the threads 1041 of the anchor bore 1040.

Figure 8:
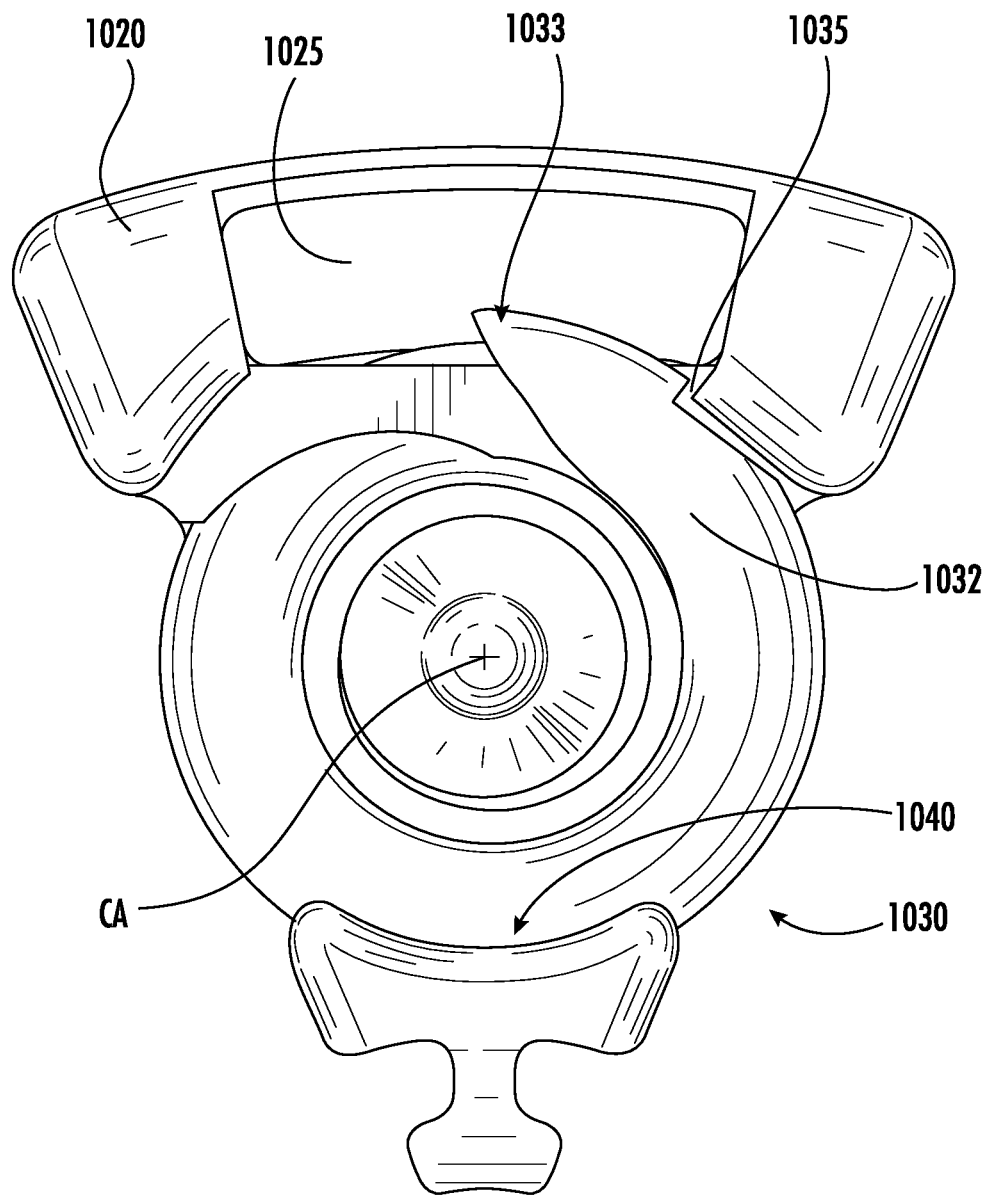
FIG. 8 is a bottom end view of an embodiment of an anchor assembly formed in accordance with various aspects of the present disclosure.

An alternate or additional manner of inhibiting or preventing further proximal advancement of the helical coil 1032 relative to the anchor housing 1020 is illustrated in FIG. 8. Instead of, or in addition to, the relation or interaction the taper or pitch of a tapered helical coil 1032 with respect to the anchor bore 1040 within the anchor housing 1020 contributing to inhibiting or preventing undesired or unintended proximal withdrawal of the anchor 1030, the configuration of the outer surface of the helical coil 1032 relative to the anchor bore 1040 may contribute to inhibiting or preventing undesired or unintended proximal withdrawal of the anchor 1030. In some embodiments, the outer surface of the helical coil 1032 is modified adjacent the distal tip 1033t thereof to interfere with the anchor housing 1020 to inhibit or to prevent further rotation of the helical coil 1032 relative to the anchor housing 1020. In some embodiments, such interference is between an outer surface of the helical coil 1032 with a portion of the anchor housing 1020 adjacent the frame slot 1025. For instance, the radial distance of the outer surface of the helical coil 1032 from the anchor housing 1020 may be modified to interfere with further rotation of the helical coil 1032 in a direction which would otherwise proximally advance the helical coil 1032. For example, as illustrated in FIG. 8, an outer portion of the helical coil 1032 may be removed (such as by shaving the material) adjacent the distal tip 1033 thereof, such as to form a notch 1035. In addition, the distance of the inner wall 1042 of the anchor bore 1023 to the coil axis CA may be varied, such that the outer diameter of the distalmost helical coil 1032 adjacent the tip 1033t of the helical coil 1032 is larger than the distance between at least one section of the anchor housing 1020 from the coil axis CA. As may be seen with reference to FIG. 8, as the helical coil 1032 is rotated to advance proximally, the notch 1035 and a portion of the anchor housing 1020 (in the illustrated example, adjacent the frame slot 1025) form a radial stop or interference stop inhibiting or preventing further rotation of the helical coil 1032. It will be appreciated that instead of removing material from an outer surface of the helical coil 1032, the outer surface of the helical coil 1032, such as adjacent the tip 1033t thereof, may be expanded to interfere with the housing to inhibit or prevent further proximal advancement of the helical coil 1032. For instance, the helical coil 1032 may be deformed (e.g., to change the cross-section of the wire or other element forming each turn of the helical coil 1032) so that an outer surface closer to the coil distal tip 1033*t* extends sufficiently outward to create the desired interference stop with the anchor housing 1020. Additionally or alternatively, material may be added to the outer surface of the helical coil 1032 adjacent the distal tip 1033*t* thereof to create the desired interference with the anchor housing 1020. Such modifications may be made in any desired manner known or heretofore known in the art, the resulting configuration being readily appreciated to those of ordinary skill in the art with requiring further detailed illustration.

Undesired distal advancement of the anchors 1030 through (and beyond or out of) the anchor housing 1020 may be prevented by abutment of an anchor head shoulder 1035 (such term may be used interchangeably herein with flange or projection or the like without intent to limit) on the anchor head 1036 with a proximal end 1021 of the anchor housing 1020, as may be appreciated with reference to FIG. 6. In some embodiments, the helical anchor 1030 may be distally advanced into the tissue until the proximal-most turn of the helical coil 1032 is positioned within the unthreaded distal section 1044 in the anchor bore 1040 of the anchor housing 1020, and the anchor shaft 1034 is within the section of the anchor bore 1040 with threads 1041. Because the helical coil 1032 is not engaged with the threads 1041 in the anchor bore 1040, further rotation of the helical anchor 1030 does not result in further distal advancement of the helical anchor 1030, but may result in tissue being drawn proximally towards the anchor housing 1020 to improve affixation of the anchor assembly 1010 to the tissue. An internal shoulder 1045 may be provided at a proximal end of the unthreaded distal section 1044 of the anchor bore 1040 to prevent or inhibit unintended or undesired proximal withdrawal of the anchor 1030 from the anchor housing 1020.

Various additional features of an implantable device as illustrated in FIGS. 1 and 2, as well as related delivery systems and methods of use may be appreciated with reference to the following patents and patent applications, each of which is incorporated herein by reference in its entirety for all purposes: U.S. Pat. No. 9,180,005, issued Nov. 10, 2015, and titled "ADJUSTABLE ENDOLUMINAL MITRAL VALVE RING"; U.S. Pat. No. 10,335,275, issued Jul. 2, 2019, and titled "METHODS FOR DELIVERY OF HEART VALVE DEVICES USING INTRAVASCULAR ULTRASOUND IMAGING"; U.S. Pat. No. 9,848,983, issued Dec. 26, 2017, and titled "VALVE REPLACEMENT USING ROTATIONAL ANCHORS"; U.S. Pat. No. 10,555,813, issued Feb. 11, 2020, and titled "IMPLANTABLE DEVICE AND DELIVERY SYSTEM FOR RESHAPING A HEART VALVE ANNULUS"; U.S. Pat. No. 10,548,731, issued Feb. 4, 2020, and titled "IMPLANTABLE DEVICE AND DELIVERY SYSTEM FOR RESHAPING A HEART VALVE ANNULUS"; U.S. Pat. No. 9,192,471, issued Nov. 24, 2015, and titled "DEVICE FOR TRANSLUMENAL RESHAPING OF A MITRAL VALVE ANNULUS"; U.S. Patent Application Publication No. 2010/0249920, published Sep. 30, 2010, and titled "DEVICE FOR TRANSLUMENAL RESHAPING OF A MITRAL VALVE ANNULUS"; U.S. Pat. No. 9,795,480, issued Oct. 24, 2017, and titled "RECONFIGURING TISSUE FEATURES OF A HEART ANNULUS"; U.S. Pat. No. 9,610,156, issued Apr. 4, 2017, and titled "MITRAL VALVE INVERSION PROSTHESES"; U.S. Pat. No. 10,321,999, issued Jun. 18, 2019, and titled "SYSTEMS AND METHODS FOR RESHAPING A HEART VALVE"; U.S. Patent Application Publication No. 2020/0022811, published Jan. 23, 2020; and/or U.S. Patent Application Publication No. 2020/0121461, published Apr. 23, 2020.

Although embodiments of the present disclosure have been described in connection with annuloplasty devices and with specific reference to mitral valves, it will be appreciated that annuloplasty devices for the tricuspid valve, as well as various other implants may similarly benefit from the devices, assemblies, systems, and methods disclosed herein.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. An anchor assembly configured to be implanted with respect to tissue, the anchor assembly comprising:
    a helical anchor with a plurality of helical turns; and
    an anchor housing;
    wherein:
    an anchor bore is defined in the anchor housing with internal threads through which the helical turns of the helical anchor extend;
    the helical anchor has a proximal end and a distal end, the distal end extending away from the anchor housing as the helical anchor is advanced distally away from the anchor housing; and
    the distalmost helical turn of the helical anchor, closest to the distal end of the helical anchor, has an outer diameter greater than a diameter of at least a distalmost internal thread of the anchor bore in which the distalmost helical turn of the helical anchor is positioned.

2. The anchor assembly of claim 1, wherein the helical anchor comprises a shaft having a proximal end and a distal end, an anchor head along a proximal end of the shaft, and a helical coil having a proximal end and a distal end and defining the helical turns of the helical anchor, the proximal end of the helical coil mounted proximate the shaft distal end.

3. The anchor assembly of claim 1, wherein the helical turns extend through openings through a side wall of the anchor housing.

4. The anchor assembly of claim 1, wherein the helical anchor has a distal end configured to penetrate tissue, and a proximal end.

5. The anchor assembly of claim 1, the outer diameter of the distalmost helical turn closest to the distal end of the helical anchor is greater than the outer diameter of more proximal helical turns closer the proximal end of the helical anchor.

6. The anchor assembly of claim 5, wherein the outer diameters of the two distalmost helical turns are greater than the outer diameter of helical turns proximal thereto.

7. The anchor assembly of claim 6, wherein the outer diameters of the two distalmost helical turns taper in a proximal direction.

8. The anchor assembly of claim 6, wherein the outer diameters of helical turns proximal to the two distalmost helical turns are substantially constant.

9. The anchor assembly of claim 6, wherein the outer diameters of the helical turns taper in a direction from the distal end to the proximal end of the helical anchor.

10. The anchor assembly of claim 4, wherein the distal end of the helical anchor has a sharpened tip to penetrate tissue.

11. An implant system configured for transluminal delivery through a patient, the implant system comprising:
    an implantable device movable between a delivery configuration for transluminal delivery to a treatment site within a patient, and an expanded configuration; and
    at least two anchor assemblies mounted on the implantable device adjacent one another, the anchor assemblies each comprising:
    a helical anchor with a plurality of helical turns; and
    an anchor housing with an anchor bore defined therein;
    wherein in the delivery configuration of the implantable device, helical turns of adjacent anchor assemblies nest with one another.

12. The implant system of claim 11, wherein the implantable device includes a frame member, and the anchor assemblies are mounted on an end of the frame member.

13. The implant system of claim 12, wherein the frame member comprises a proximal end and a distal end, the distal end including a plurality of distal apices, the at least two anchor assemblies being mounted on adjacent distal apices of the frame member.

14. The anchor assembly of claim 13, wherein:
    the helical anchor has a proximal end and a distal end, the distal end extending away from the anchor housing as the helical anchor is advanced distally away from the anchor housing; and
    the outer diameter of the distalmost helical turn closest to the distal end of the helical anchor is greater than the outer diameter of helical turns closer the proximal end of the helical anchor.

15. The implant system of claim 14, wherein:
    the anchor housing includes a frame slot for receiving a distal apex of the frame member;
    the anchor housing as an inner diameter;
    the distalmost turn of the helical anchor has an outer diameter greater than the anchor housing inner diameter such that the distalmost turn extends into the frame slot; and the distal apex is positioned in the frame slot proximal to the distalmost turn of the helical anchor when the distalmost turn of the helical anchor is positioned extending into the frame slot.

16. The anchor assembly of claim 11, wherein:
the helical anchor has a proximal end and a distal end, the distal end extending away from the anchor housing as the helical anchor is advanced distally away from the anchor housing; and
the outer diameter of the distalmost helical turn closest to the distal end of the helical anchor is greater than the outer diameter of helical turns closer the proximal end of the helical anchor.

17. The implant system of claim 11, wherein:
the anchor bore has internal threads through which the helical turns of the helical anchor extend; and
the distalmost helical turn has an outer diameter greater than a diameter of at least a portion of the anchor bore.

18. The implant system of claim 11, wherein the helical turns extend through openings through a side wall of the anchor housing.

19. A method of delivering an implantable device in a compact delivery configuration transluminally within a patient, the method comprising:
mounting at least two anchor assemblies adjacent one another on an implantable device, each anchor assembly comprising an anchor housing and a helical coil, the implantable device having an outer diameter which may be varied between a delivery outer diameter and a larger expanded outer diameter; and
moving the implantable device into the delivery configuration with the helical coils of adjacent anchor assemblies nesting with one another.

20. The method of claim 19, wherein:
the helical anchor of each of the anchor assemblies has a proximal end and a distal end, the distal end extending away from the anchor housing as the helical anchor is advanced distally away from the anchor housing; and
the distalmost helical turn of the helical anchor, closest to the distal end of the helical anchor, has an outer diameter greater than a diameter of at least a portion of the anchor bore.

* * * * *